United States Patent [19]

Iglesias

[11] 4,134,406
[45] Jan. 16, 1979

[54] CUTTING LOOP FOR SUCTION RESECTOSCOPES

[76] Inventor: Jose J. Iglesias, 1341 North Ave., Elizabeth, N.J. 07208

[21] Appl. No.: 840,247

[22] Filed: Oct. 7, 1977

Related U.S. Application Data

[63] Continuation of Ser. No. 733,896, Oct. 19, 1976, abandoned.

[51] Int. Cl.² ............................................. A61B 17/32
[52] U.S. Cl. ................................................. 128/303.15
[58] Field of Search ....................... 128/303.15, 303.14, 128/4, 7, 6; 308/4 R

[56] References Cited

U.S. PATENT DOCUMENTS

| 2,008,525 | 7/1935 | Wappler | 128/303.15 |
| 3,752,159 | 8/1973 | Wappler | 128/303.15 |
| 3,835,842 | 9/1974 | Iglesias | 128/303.15 |
| 3,901,242 | 8/1975 | Storz | 128/303.15 |

FOREIGN PATENT DOCUMENTS 1548389 12/1968 France .................................. 128/303.15

Primary Examiner—Robert W. Michell
Assistant Examiner—Arthur S. Rose
Attorney, Agent, or Firm—Scrivener, Parker, Scrivener & Clarke

[57] ABSTRACT

In a resectoscope of the type having inflow and outflow conduits and in which suction is applied to the outflow conduit, a damaged cutting loop must be replaced by blind insertion of the new loop through the annular passage between the tube which surrounds and holds the telescope and the tube which forms the inner boundary of the outflow conduit, and into the opening of a passage through the fixed block of working element. Such insertion is facilitated by the present invention by the addition to the stem of the loop of a member of arcuate cross section having its axis parallel to the stem of the loop, which is positioned adjacent the proximal end of the stem and which engages and at least partially surrounds the tube which surrounds the telescope and which positions and guides the stem of the loop as it is inserted.

1 Claim, 3 Drawing Figures

CUTTING LOOP FOR SUCTION RESECTOSCOPES

CROSS-REFERENCE TO RELATED APPLICATIONS

This application is a continuation of my co-pending application Ser. No. 733,896, filed Oct. 19, 1976, for Improved Cutting Loop For Suction Resectoscope, now abandoned.

BACKGROUND OF THE INVENTION

A resectoscope of the type with which the invention is particularly useful is disclosed and claimed in my U.S. Pat. No. 3,835,842 and, as illustrated in FIG. 1 in pertinent part, comprises the elongated tubular sheath 2 which is open at its distal end, and the tube 4 which is concentric with and within the sheath and with it forms an annular space 6 which provides the outflow conduit of the instrument. Within and concentric with and spaced inwardly from the tube 4 is the telescope stem 8 which is engaged and surrounded substantially throughout its length by the supporting tube 10. The space 12 between the tubes 4 and 10 and the telescope 8 provides the inflow conduit of the instrument. The instrument also includes a cutting loop 20 having stem 22 through which an electrically conductive wire 24 extends which protrudes from the distal end of the stem to provide spaced parallel arms 26 which are positioned on opposite sides of the telescope stem and at their distal ends are connected by the depending bare wire cutting loop 28. The proximal part of the stem of the cutting loop passes through a passage 29 in the locking block 30 of the working element and into the movable member 32 of the working element where the wire 24 engages the external electrical connection 34. The passage 29 is conventionally located at the six o'clock position in the block 30 and in the movable member 32 of the working element 32.

At the distal end of stem 22 of the cutting loop there is conventionally provided a preferably cylindrical tube 38 which is connected superiorly to the distal end of the stem and extends longitudinally thereof and surrounds the tube 10 which engages and supports the stem of the telescope, thereby to provide means for guiding the cutting loop in its longitudinal movement as it is reciprocated during the use and operation of the resectoscope. The guide 38 may be modified to provide means for stabilizing and strengthening the arms of the cutting loop, as described and claimed in my co-pending application for U.S. Pat. Ser. No. 219,687 for Stabilized Cutting Loop For Resectoscopes, and in Wappler U.S. Pat. No. 3,752,159. These described parts of the instrument do not form part of this invention.

In the course of a transurethral (TUR) procedure the arms 26 or the depending wire loop 28 of the cutting loop may be damaged, necessitating replacement of the entire cutting loop. In order to do this the sheath is left within the patient and the other part of the instrument which constitutes the working element, is withdrawn from the sheath and the damaged cutting loop is removed and replaced with a new cutting loop. It is very easy to withdraw the damaged loop, but it is very difficult to insert a new loop, as the annular space 12 through which the stem of the loop must be passed to the opening 29 in block 30 is very small and it is difficult to locate the opening as it cannot be seen. A material amount of time is therefore often required to make this blind insertion of the new loop.

It has therefore been the object of this invention to provide means for guiding the stem along and through the annular space 12 to the passage 29 in the block 30 of the working element, so that a new loop may be quickly and accurately put into position when it is necessary to do so.

SUMMARY OF THE INVENTION

The stem of a cutting loop which forms part of a resectoscope is provided adjacent its proximal end with a member which is arcuate in cross sectional shape, the axis of which is parallel to that of the stem, and which engages and partially surrounds the tube which surrounds the telescope stem, and which guides the proximal end of the stem of the cutting loop as it is moved into and along and through the annular space between that tube and the tube which forms the inner boundary of the outflow conduit, and into the passage through the block of the working element of the resectoscope.

DESCRIPTION OF THE INVENTION

Figure 1:
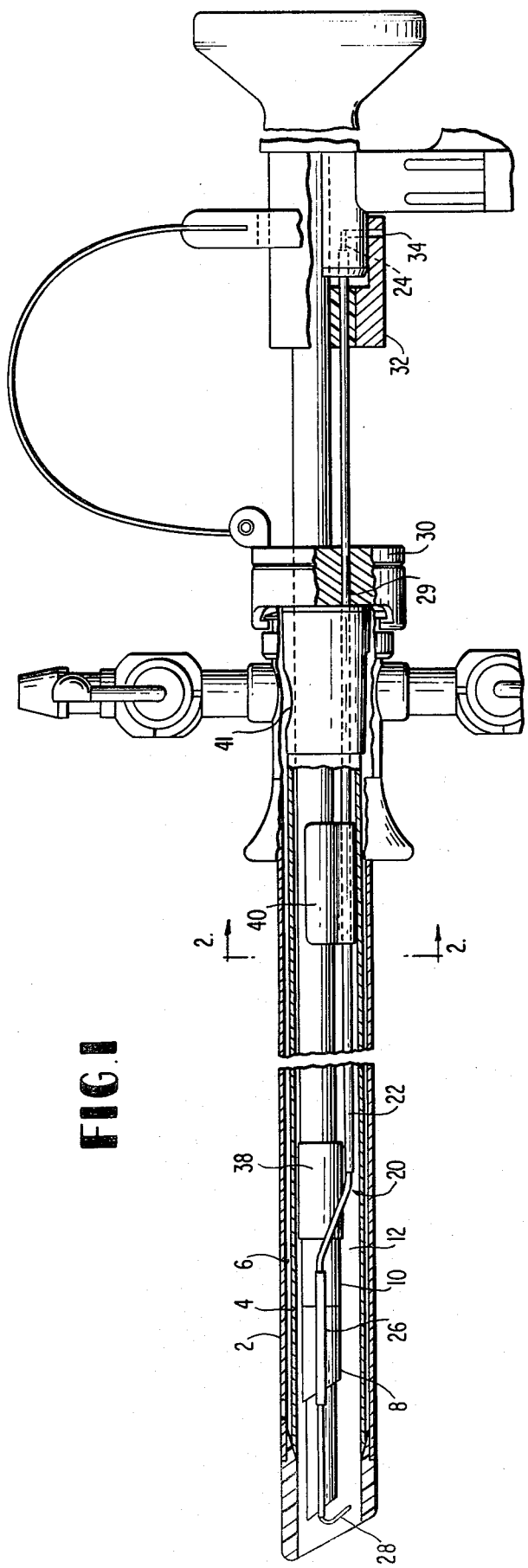
FIG. 1 is a longitudinal sectional view of a resectoscope of the type with which the invention is useful, with parts broken away, showing the cutting loop and the guide provided by the invention associated therewith.
Figure 2:
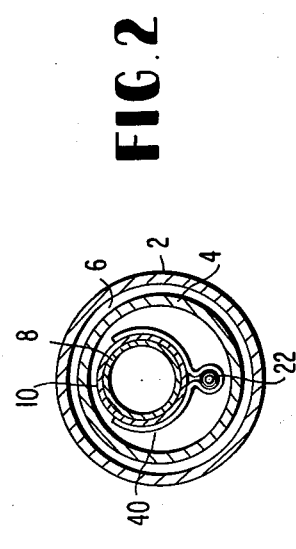
FIG. 2 is an enlarged cross sectional view taken on line 2—2 of FIG. 1.
Figure 3:
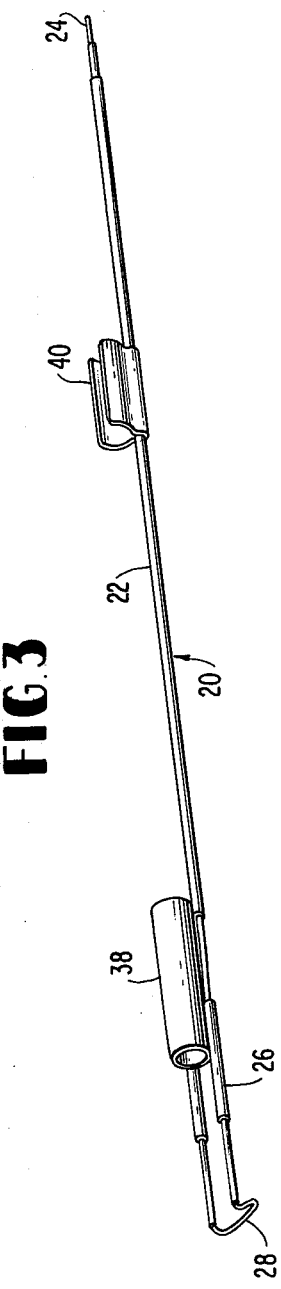
FIG. 3 is a perspective view showing a cutting loop with the guide means provided by the invention.

The guide member 40 provided by the invention is connected superiorly to the stem 22 of the cutting loop 20 at a position proximal of the guide tube 38 and at a sufficient distance from the proximal end of the stem so that the proximal end of the guide member 40 is closely adjacent to, but does not engage or otherwise interfere with, the inner port 41 of the entrance to the inflow conduit 12 or engage the distal end of the locking block 30 of the working element of the resectoscope.

The guide member 40 is generally arcuate in cross sectional shape with its axis parallel to that of the stem of the cutting loop, and is preferably formed of rigid material, which may be metal, synthetic plastic or the like. The word "arcuate" as used in this specification and in the claim will be understood to refer generically to guide members having such a cross sectional shape that the guide member will at least partially surround the tube 10, regardless of the initial cross sectional shape of the guide member, when the stem of the cutting loop is in place in the annular space 12 of the operative instrument.

The guide member may be provided on a cutting loop of any type or construction, such as a cutting loop having a single stem, a cutting loop having a double stem, or a cutting loop having a single stem at the proximal end of the loop which branches into two stems at a point close to the proximal end of the loop. As the specific structures of these various types of cutting loops do not form part of this invention they are not illustrated in the drawings or further described in this specification.

If is becomes necessary to replace the cutting loop during a TUR procedure the sheath of the resectoscope is left within the patient and the other part known as the working element is withdrawn from the sheath and the damaged cutting loop is removed by withdrawing it from the distal end of the withdrawn assembly through the annular space 12 between tubes 4 and 10. The proximal end of a new loop is now inserted blind into the same annular space 12 in the general six o'clock position, and as it is inserted the arcuate guide member 40 at least partially surrounds the tube 10 which surrounds the telescope. As the loop is pushed into the space 12 the guide member slides along tube 10 and thereby guides the proximal end of the stem of the loop to the opening into passage 29 in block 30. Once within the passage the stem is guided directly to the opening in the movable block 32 and the electrical contact 36. The arcuate cross sectional shape of the guide member causes the member to engage the sides of tube 10 and thus prevent lateral movement of the stem of the loop as it moves along annular space 12.

I claim:

1. A cutting loop for a resectoscope of the type which includes an elongated tubular sheath having distal and proximal ends, a first tube within and concentric with and spaced from the sheath and defining with the sheath an elongated annular outlet conduit for fluid from the operative field, an optical telescope within and concentric with the first tube and extending longitudinally thereof, and a second tube surrounding and engaging the telescope to provide support to it and defining with the first tube an annular passage for clear fluid flowing to the operative field, the cutting loop comprising;

a. an elongated stem adapted to be positioned below and parallel to the second tube for longitudinal movement in a direction parallel thereto,
b. an electrode wire including:
 (1.) a first part extending through and electrically insulated from the inner surface of the stem,
 (2.) a generally loop-shaped second part extending beyond the distal end of the stem and comprised of:
  i. a pair of spaced electrically insulated arms adapted to extend along opposite sides of the telescope, and
  ii. an uninsulated cutting element constituting a continuation of each arm and position in the field of vision of the telescope,
c. a tubular member mounted superiorly on the distal end of the stem with its axis parallel to the stem and adapted to surround and engage the second tube to guide the cutting loop in its longitudinal reciprocating movement, and
d. guide means for slidably maintaining the stem in spaced relation to the second tube during sliding insertion of the cutting loop into a resectoscope, comprising a member of arcuate cross sectional shape secured to the stem superiorly thereof with its axis parallel to the stem, the cross sectional size and shape of the member being such that its inner surface will be in contact with and surround the outer surface of the second tube sufficiently to prevent lateral movement of the stem with respect to the second tube during such insertion, the member being positioned proximal to the tubular member mounted on the distal end of the stem.

* * * * *